United States Patent [19]

Stewart et al.

[11] 3,954,709
[45] May 4, 1976

[54] PHENYLETHYL GROUP CONTAINING RESINS FOR THE SYNTHESIS OF PEPTIDES

[75] Inventors: John M. Stewart, Denver; Gary R. Matsueda, Aurora, both of Colo.

[73] Assignee: The Regents of the University of Colorado, Boulder, Colo.

[22] Filed: May 29, 1973

[21] Appl. No.: 364,908

[52] U.S. Cl. .............. 260/47 UA; 260/112.5 R; 526/336; 526/310
[51] Int. Cl.² .............. C08F 12/08; C08F 12/36
[58] Field of Search .............. 260/88.1 P, 88.1 PN, 260/47 UA, 88.2 C

[56] References Cited
UNITED STATES PATENTS

| | | | |
|---|---|---|---|
| 2,588,968 | 3/1952 | Dickey et al. | 260/558 |
| 2,631,999 | 3/1953 | McMaster et al. | 260/88.1 |
| 2,788,330 | 4/1957 | Gilwood et al. | 260/2.1 |
| 3,078,185 | 2/1963 | Kine et al. | 117/141 |
| 3,645,996 | 2/1972 | Southard | 260/88.2 |

*Primary Examiner*—Lester L. Lee
*Attorney, Agent, or Firm*—Burton, Crandell & Polumbus

[57] ABSTRACT

The phenylethyl group,

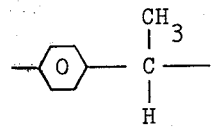

in polymer carriers for the synthesis of peptides and peptide amides, particularly polymer carriers such as styrene-1% divinyl benzene polymers for use in solid phase peptide synthesis.

20 Claims, No Drawings

PHENYLETHYL GROUP CONTAINING RESINS FOR THE SYNTHESIS OF PEPTIDES

The invention described herein was made in the course of work under a grant or award from the Department of Health, Education and Welfare.

BACKGROUND OF THE INVENTION

The present invention relates to compounds containing the α phenylethyl group finding particular, but not necessarily exclusive, utility in the synthesis of peptides, and more specifically in the solid phase synthesis of peptides. More particularly, the present invention relates to the use of phenylethyl compounds as applied to polymer carriers for the synthesis of peptides and peptide amides, particularly in connection with the solid phase synthesis thereof.

Peptide synthesis has been greatly facilitated by the development of solid phase peptide synthesis (SPPS) in which peptide chains are assembled on an insoluble polymer bead as a carrier. An automated mechanism for the solid phase synthesis of peptides is disclosed in U.S. Pat. No. 3,531,258, issued Sept. 29, 1970, to R. B. Merrifield, J. M. Stewart and N. Jernberg for "APPARATUS FOR THE AUTOMATED SYNTHESIS OF PEPTIDES". In the solid phase peptide synthesis, the bond which holds the first amino acid to the polymer carrier is an extremely important one. Currently available bonds for the synthesis of simple peptides involve a benzyl ester linkage, while those for the synthesis for peptide amides, which are utilized in connection with many hormones, involves a benzhydryl amide linkage. One of the principal problems is that the bonds formed on currently available carrier resins are so stable that the conditions needed to sever the peptide from the carrier are so drastic that damage occurs to the peptide.

The solid phase synthesis of peptides is extensively described by John M. Stewart and Janis D. Young in "Solid Phase Peptide Synthesis" published by W. H. Freeman & Company, San Francisco 1969. Stewart and Young describe the chemistry of solid phase peptide synthesis, laboratory techniques and apparatus, and the book includes extensive appendixes on apparatus, chemicals and reagents, amino acids, protecting groups and reagents, and a bibliography of references. Stewart and Young describe in detail the chemical aspects of the resin support and many protecting groups. Where necessary for a more complete understanding of the present invention, reference should be made to the Stewart and Young book, and such book is by reference incorporated herein.

OBJECTS OF THE INVENTION

The principal object of the present invention is to provide an improved carrier polymer resin and improved blocking groups for use in peptide synthesis.

More particularly, it is an object of the invention to provide an improved resin carrier for use in the solid phase synthesis of peptides which carrier is of less bulk and of greater lability than polymer carriers heretofore known or utilized.

SUMMARY OF THE INVENTION

The compounds of the present invention may be characterized generally as phenylethyl group containing compounds having the general formula

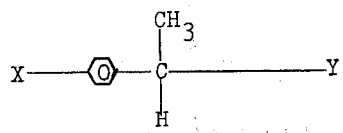

wherein:
X is a polymer or polymer backbone (sometimes referred to by the symbol (P—), and Y is —NH$_2$, —OH, —Cl, —Br The present invention is more particularly concerned with the use of the phenylethyl group, to wit:

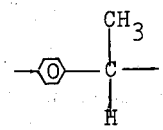

in polymer carriers for the synthesis of peptides and peptide amides, and particular polymer carriers for use in solid phase peptide synthesis.

DESCRIPTION OF THE PREFERRED EMBODIMENTS

Polymers for the Synthesis of Peptides and Peptide Amides

The synthesis of peptides and peptide amides utilizing polymer support or carrier substances, both soluble and insoluble, are known in the art. While the present invention is believed to be applicable to the use of the phenylethyl group in polymers, both soluble and insoluble, particular reference will be made to the solid phase synthesis of peptides utilizing a suitable insoluble support polymer carrying a phenylethyl group as the means of attaching the amino acid to the polymer. More particularly, the preferred polymer is a copolymer of styrene and divinylbenzene with the latter present in an amount of approximately 1 to 2 percent as a cross-linking agent. The polymer is utilized in the form of beads or particulate solids having a mesh size of between 200 and 400 mesh. In this specification, the low cross-linked styrene divinylbenzene co-polymer will be referred to generally as the styrene-1%-divinylbenzene or S-1%DVB polymer, and where applicable, the symbol for the S-DVB polymer or other polymer carriers will be

with the benzene ring representing the phenyl groups of the styrene and the (P) representing the polymer backbone. The symbols are of general form, however, in that any suitable polymer might be utilized with either self-contained or added phenyl groups, which will ultimately form a part of the phenylethyl groups embodying the present invention. As an example of the latter, the styrene-DVB polymer may be first modified to form a phenoxymethyl styrene-DVB co-polymer. The phenyl groups of the styrene are modified by attaching, in the para-position, a phenoxymethyl group, and the phenyl radical on the latter is then converted to a phenylethyl group.

To illustrate the present invention, beads of cross-linked polystyrene-DVB are modified chemically by acetylation with acetyl chloride in the presence of a Friedel-Crafts catalyst to form a ketone,

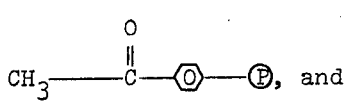, and the methyl ketone thus formed is reacted with formamide by a Leuckart reaction to form the amide by reductive amination:

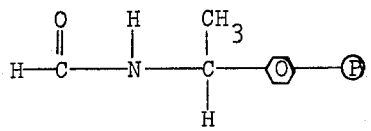

The latter is then acidified and neutralized to form the phenylethyl amine modified polystyrene-DVB polymer:

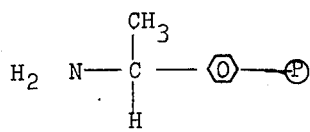

Similarly, an ether group may be introduced into the resin by chloromethylation of the phenyl groups followed by a reaction with sodium phenoxide. The phenyl radical of the phenoxymethyl polystyrene-DVB is then acetylated as described above. After amination, acidification and neutralization, the phenylethyl amine phenoxymethyl polystyrene-DVB results:

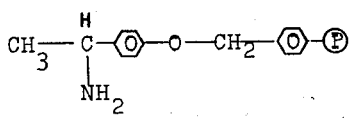

By standard procedures, a peptide is assembled onto the amino group of the resin carrier thus produced. See the Stewart and Young work, supra. After formation of the desired peptide, it is removed as an amide by the use of liquid HF:

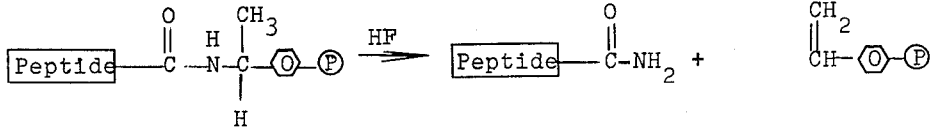

Where it is desired to synthesize peptides having free terminal carboxyl groups, acetylation of the styrene-DVB co-polymer, followed by reduction of the ketone to the hydroxyl, results in a carrier resin to which a blocked amino acid may be secured by utilization of a diimide such as dicyclohexylcarbodiimide. Alternatively, the functional hydroxyethyl group may be converted to a halide such as a bromide or chloride, which in turn is esterified with an α-carboxyl group of a blocked amino acid.

The following examples illustrate the preparation of carrier polymers including the phenylethyl group of the present invention.

EXAMPLE I

Phenoxymethyl polystyrene-1% divinylbenzene:

To a stirred solution of 3.76g of phenol in 50ml dry dimethyl sulfoxide, under nitrogen bubbling and chilling, is added 1.8g sodium hydride in oil. To the sodium phenoxide solution is added 5g of chloromethylated poly(styrene-1% divinylbenzene) in the form of 200–400 mesh beads, and containing 0.75 meq chlorine per g. The suspension is heated at 80°, with continued stirring and nitrogen bubbling, for 10 hr. The resin is filtered off and washed thoroughly with acetic acid-water, ethanol-water, ethanol, chloroform, and ethanol, and then dried.

Acetyl phenoxymethylpolystyrene-1% divinylbenzene

To a stirred suspension of 20g of the phenoxymethyl-polystyrene-1% divinylbenzene produced according to Example I, in 200 ml dry carbon disulfide at 0°, is added 1.1ml of acetyl chloride in 100 ml carbon disulfide, and 4.9 ml of stannic chloride in 800 ml carbon disulfide. After stirring for 30 min at 0°, the mixture is poured into ethanol, and the resin is filtered off and washed with ethanol, dioxane-hydrochloric acid, ethanol-water, ethanol, chloroform, and methanol.

EXAMPLE II.

Acetyl polystyrene-1% divinylbenzene

To a stirred suspension of 20g of beads (200–400 mesh) of poly(styrene-1% divinylbenzene) in 150 ml of dry carbon disulfide is added 1.4 ml of acetyl chloride and 2.92g anhydrous aluminum chloride. The mixture is stirred for 30 min at room temperature and then refluxed with stirring for 2 hr. The resin is filtered, and washed well with ethanol and then dioxane-hydrochloric acid.

EXAMPLE III

Conversion of acetyl polymer to amine polymer hydrochloride salt

Into a flask fitted with a stirrer, a reflux condenser, a water separator, and a thermometer for measurement of internal temperature, is placed 5g of acetylated resin of Example I or II. 50 ml nitrobenzene, 12.6g ammonium formate, 8.0 ml formamide and 10ml of 88% formic acid. The mixture is heated with stirring at an internal temperature of 165°–170° for 6 hr. After the initial 2.5 hr of heating, an additional 10 ml of 88% formic acid is added to the mixture. The mixture is cooled, and the resin is filtered off and washed well with ethanol. The resin is then heated under reflux for 2 hr. with a 1:1 mixture of ethanol and concentrated hydrochloric acid. The resin is filtered off, washed with ethanol-water, ethanol, chloroform and methanol, and then dried.

EXAMPLE IV

1-Hydroxyethyl polystyrene-1 divinylbenzene.

A mixture of 10g acetyl polystyrene-1% divinylbenzene beads of Example II, 100 ml dry dimethyl formamide and 1.15g sodium borohydride is heated under reflux for 4 hr. The mixture is cooled and the resin filtered off and washed with dimethyl formamide. The resin is treated for 20 min with a mixture of dimethyl formamide and concentrated hydrochloric acid at room temperature, washed thoroughly with water, ethanol-water, ethanol, chloroform and methanol, and then dried.

The resins of Examples III and IV may be utilized in the solid phase synthesis of peptides in accordance with standard literature methodology. It will be noted that the resins disclosed in these examples each include the phenylethyl group described above.

After forming a peptide on the phenylethyl substituted carrier resin, the peptide is removed as the amide in the case of an amino resin, and as an acid in the case of the hydroxy resin. The techniques for forming peptides on the polymer are standard and described in some detail in the Stewart and Young book, supra. An advantage of the phenylethyl group on the resin support is the lability of the peptide to removal under relatively mild conditions without affecting the peptide linkages. For example, a peptide amide can be removed from a phenylethyl amine support by the use of anhydrous hydrogen fluoride, resulting in the formation of a peptide amide and leaving the resin support with an ethylene double bond. Formation of the resonance-stabilized double bond gives a strong driving force to the separation reaction. A similar resonance-stabilized double bond results from the use of a hydroxyphenylethyl group, resulting in a peptide having free carboxyl groups.

Current technology for the solid phase peptide synthesis of peptide amides utilizes in addition to the chloromethyl group described by Stewart and Young the benzhydrylamine S-DVB resins:

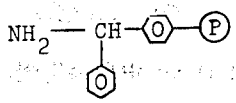

which, as will be noted, includes a symetrical carbon having two phenyl groups connected therewith. Where it is desired to introduce bulky amino acids such a resin carrier, steric hindrance is encountered thereby making it difficult to utilize the benzhydrylamine resins with bulky amino acid reactions. With the phenylethyl group of the present invention on the other hand, steric hindrance is not encountered by virtue of the methyl group. The effectiveness of the phenylethyl group can be further enhanced by inserting the phenoxymethyl linkage between the asymetric carbon and the phenyl group of the S-DVB resin.

While certain illustrative embodiments of the present invention have been described in considerable detail, it should be understood that there is no intention to thereby limit the present invention. On the contrary, it is the intention to cover all modifications, equivalents and uses of the present invention as fall within the spirit and scope of the invention as expressed in the appended claims.

We claim:

1. For use in the solid phase synthesis of peptides, a solid particulate support resin consisting essentially of cross-linked polystyrene-divinylbenzene copolymer having a phenylethyl group in the para position on at least a portion of the phenyl groups of the polystyrene.

2. Solid, cross-linked p-(α-aminoethyl) polystyrene-1% divinylbenzene.

3. Solid, cross-linked p-(α-hydroxyethyl) polystyrene-1% divinylbenzene.

4. Solid, cross-linked p-(α-aminoethyl) phenoxymethyl polystyrene-1% divinylbenzene.

5. A solid particulate resin having the general formula

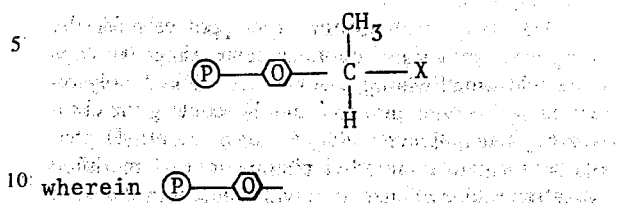

wherein ⓟ—Ⓞ— represents a solid polystyrene-1% divinylbenzene polymer having depending phenyl groups at least a portion of which carry an ethyl group in the para position, and X is —NH$_2$, —OH, —Cl, or —Br.

6. A solid crosslinked polystyrene-1% divinylbenzene copolymer resin wherein at least a portion of the phenyl groups of the polystyrene carry in the para position a radical selected from the group consisting of

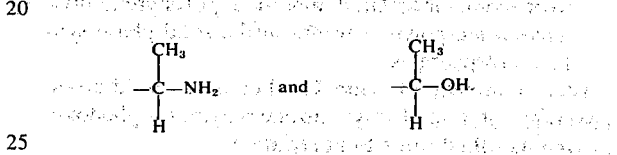

7. A solid phenylethyl polymer support resin having the general formula

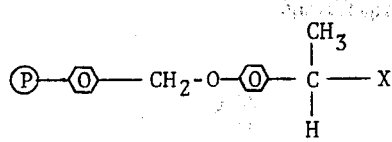

wherein ⓟ—Ⓞ⟩ represents a solid polystyrene-1% divinylbenzene polymer having depending phenyl groups at least a portion of which carry an ethyl group in the para position, and X is —NH$_2$, —OH, —Cl, or —Br.

8. The method of forming a support resin for the solid phase synthesis of peptides comprising the steps of:
   a. reacting a solid cross-linked polystyrene-divinylbenzene polymer with acetyl chloride to form a methyl ketone modified polymer;
   b. reacting the methyl ketone modified polymer with formamide to form an ethyl amide modified polymer; and
   c. hydrolyzing and neutralizing the phenylethyl amide modified polymer to form an aminoethyl modified polystyrene-divinylbenzene polymer useful in the solid phase synthesis of peptides.

9. The method of forming a support resin for the solid phase synthesis of peptides comprising the steps of:
   a. chloromethylating a solid cross-linked polystyrene-divinylbenzene polymer;
   b. reacting the chloromethylated polymer with sodium phenoxide to form a phenoxymethyl modified polymer;
   c. reacting the phenoxymethyl modified polymer with acetyl chloride to form a methyl ketone phenoxymethyl modified polymer;
   d. reacting the methyl ketone phenoxymethyl modified polymer with formamide to form an ethyl amide phenoxymethyl modified polymer; and
   e. hydrolyzing and neutralizing the ethylamide phenoxymethyl modified polymer to form an aminoethyl phenoxymethyl modified polystyrene-divinylbenzene polymer useful in the solid phase synthesis of peptides.

10. The method of forming a suppot resin for the solid phase synthesis of peptides comprising the steps of: a. chloromethylating a solid cross-linked polystyrene-divinylbenzene polymer; and b. reacting the chloromethylated polymer with p-(1-formamidethyl) phenol to form an aminoethyl phenoxymethyl modified polystyrene-divinylbenzene polymer useful in the solid phase synthesis of peptides.

11. The method of forming a support resin for the solid phase synthesis of peptides comprising the steps of:
   a. acetylating a solid cross-linked polystyrene-divinylbenzene polymer to form a methyl ketone modified polymer; and
   b. reducing the methyl ketone modified polymer to form an hydroxyethyl modified polystyrene-divinylbenzene polymer useful in the solid phase synthesis of peptides.

12. The method of claim 11 wherein the solid cross-linked polystyrene-divinylbenzene polymer is phenoxymethyl modified prior to acetylation.

13. A solid resin comprising a polystyrene polymer wherein at least a portion of the phenyl groups of the polystyrene carry in the para position a radical having the general formula

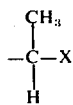

where X is —NH$_2$, —OH, —Cl, or —Br.

14. A solid resin as defined in claim 13 wherein said polystyrene polymer is a cross-linked polystyrene-1% divinylbenzene copolymer.

15. A solid resin as defined in claim 14 wherein X is —NH$_2$.

16. A phenylethyl composition having the formula

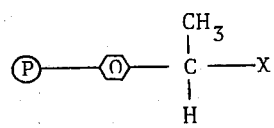

wherein 

represents a solid polymer having depending phenyl groups, at least a portion of which carry the ethyl radical, and X is —NH$_2$, —OH, —Cl, or —Br.

17. A phenylethyl composition as defined in claim 13 wherein

represents solid polystyrene.

18. A phenylethyl composition as defined in claim 13 wherein represents solid crosslinked polystyrene-1% divinylbenzene.

19. A phenylethyl composition as defined in claim 15 wherein X is —NH$_2$.

20. A phenylethyl composition as defined in claim 15 wherein X is —OH.

* * * * *